US005320104A

United States Patent [19]

Fearnside et al.

[11] Patent Number: 5,320,104

[45] Date of Patent: Jun. 14, 1994

[54] TRANSESOPHAGEAL ULTRASOUND PROBE

[75] Inventors: James Fearnside, Lexington; Wojtek Sudol, Burlington, both of Mass.

[73] Assignee: Hewlett-Packard Company, Palo Alto, Calif.

[21] Appl. No.: 979,553

[22] Filed: Nov. 18, 1992

Related U.S. Application Data

[63] Continuation of Ser. No. 686,919, Apr. 17, 1991, abandoned.

[51] Int. Cl.[5] .......... A61B 8/12

[52] U.S. Cl. .......... 128/661.01; 128/662.03; 128/662.06

[58] Field of Search .......... 128/660.1, 661.01, 662.03, 128/662.04, 662.06

[56] References Cited

U.S. PATENT DOCUMENTS

| | | | |
|---|---|---|---|
| 3,779,234 | 12/1973 | Eggleton et al. | 128/2 |
| 4,305,014 | 12/1981 | Borburgh et al. | 310/334 |
| 4,310,957 | 1/1982 | Sachs | 29/25.35 |
| 4,460,841 | 7/1984 | Smith et al. | 310/334 |
| 4,471,785 | 9/1984 | Wilson et al. | 128/661.01 |
| 4,543,960 | 10/1985 | Hanui et al. | 128/662.06 |
| 4,640,291 | 2/1987 | Hoen | 128/660 |
| 4,671,293 | 6/1987 | Shaulov | 128/661.01 |
| 5,176,142 | 1/1993 | Mason | 128/662.06 |
| 5,181,514 | 1/1993 | Solomon et al. | 128/662.06 X |
| 5,226,422 | 7/1993 | McKeighen et al. | 128/662.06 |

FOREIGN PATENT DOCUMENTS

| | | |
|---|---|---|
| 006623 | 6/1979 | European Pat. Off. . |
| WO92/02180 | 2/1992 | PCT Int'l Appl. . |

OTHER PUBLICATIONS

"Probe for Rectal Echography", EP 0320331 Published Jun. 1989, to Souquet et al.

Bom, N. et al., "Early and Recent Intra-Luminol Ultrasound Devices", Intnl. Journal of Cardiac Imaging, vol. 4, pp. 79–88 1989.

Smith, W. A. et al. "Properties of Composite Piezoelectric Materials for Ultrasonic Transducers", IEEE UTS Symp. Proc., Nov. 14–16, 1984.

Hanrath, P. et al. "5 Clinical Implications of Transesophageal Echocordiography-Present Status: Future Aspects", in *Advances in Non-Invasive Cardiology*, ®1983 Martinus Nijhoff Publ., Boston ISBNO-89838-576-8 pp. 31–37.

Hanrath, P. et al., "Transesophageal Echo Cardiography", Cardiography Department, Eppendorf University Hospital, pp. 1–27.

Schlüter, M., "Transesophageal cross-sectional echocardiography with a phased array transducer system", Apr. 1982, Br Heart F, vol. 48: 67–72.

*Primary Examiner*—Francis Jaworski

[57] ABSTRACT

An endoscopic ultrasound probe for use in transesophageal echo cardiography comprises a rotatable ultrasound transducer array for obtaining two-dimensional cross-sectional images along a variety of scan planes. The array is formed of a plurality of transducer elements and rotates about an axis perpendicular to the plane of the transducer elements. The rotating array defines a circular region of rotation and has a surface area which substantially matches the area of the circular region of rotation within the probe. More specifically, the elements of the array have varying mechanical lengths such that the rotatable array may have a circular shape, a substantially circular shaped or an N-sided polygonal shape where N is an integer greater than four.

12 Claims, 4 Drawing Sheets

TRANSESOPHAGEAL ULTRASOUND PROBE

This is a continuation of co-pending application Ser. No. 07/686,919 filed on Apr. 17, 1991 and now abandoned.

BACKGROUND

Transesophageal echo (TEE) cardiography is an established technique in the area of cardiac imaging and involves the insertion of an ultrasound probe into a subject's esophagus to scan the heart from inside the esophagus. The ultrasound probe employs a transducer array to obtain a two-dimensional cross-sectional image of the subject's heart.

An ultrasound TEE probe having a rotatable transducer array for obtaining cross-sectional images of the heart along a variety of scan planes is well known. In "Transoesophageal Cross-Section Echocardiography With A Phased Array Transducer System" by Schluter et. al., an ultrasound probe having a rotatable array is suggested for obtaining an improved assessment of left ventricular morphology. Another TEE probe having a rotatable array is described in U.S. Pat. No. 4,543,960 to Harui et al.

SUMMARY OF THE INVENTION

The present invention comprises an endoscopic ultrasound TEE probe for use with remote ultrasound electronics in transesophageal echo cardiography. The probe comprises a rotatable ultrasound transducer array for obtaining two-dimensional cross-sectional images along a variety of scan planes. The array is formed of a plurality of transducer elements arranged in a plane and is supported in an inner volume. The array rotates about an axis perpendicular to the plane of the array elements.

The invention resides in recognizing the need to maximize the transmitting/receiving surface of an array within the limited confines of a TEE probe, and the realization that this result can be attained by choosing an array having a surface area which closely matches that of a circle defined by rotation of the greatest radius of the array. In accordance with the present invention, the elements of the array have varying mechanical lengths such that the surface area of the array is maximized for a small probe size. More specifically, a rotating array defines a circular region of rotation having a radius R and having a surface area in the plane of the elements equal to $\pi R^2$. A conventional rectangular array has a transmitting/receiving surface area of no more than $2R^2$, where R is one half its diagonal and thus the greatest radius from the center of rotation. Therefore, the surface area of the conventional is less than 64% of the area of the circle defined by the rotation of the rectangular array. The preferred array is circular to provide 100% utility of the circular region required for its rotation. Another embodiment comprises a substantially circular array having two flat edges symmetrically disposed along the its periphery. The substantially circular array provides at least 90% utility of the circular region of rotation. Further, improvement over the conventional array may be obtained with an N-sided polygon, where N is an integer greater than four. For example, a pentagonal array increases the percentage of utilized area to about 76%, and a hexagonal array increases that percentage to about 83%. Of the polygons, a hexagon, or other polygon of an even number of sides, is preferred because it provides dual symmetry. Dual symmetry is characterized as symmetry relative to a first axis extending along the length of the array as well as symmetry relative to a second axis extending along another length of the array, the second axis being perpendicular to the first axis and intersecting the first axis at the center of the array.

The circular-shaped array, the substantially circular-shaped array and the polygonal-shaped arrays are easily machined. However, other shapes which substantially match the circle of rotation, particularly those covering over 80% of the total area, may be used. However, the circular array is most preferred because it provides 100% utilization of the circular region of rotation, providing a symmetric and smoothly varying array which is most easily machined.

BRIEF DESCRIPTION OF THE DRAWINGS

In the enclosed drawings like reference characters refer to the same parts throughout the different views. The drawings are not necessarily to scale, emphasis instead being placed upon illustrating the principles of the invention.

DETAILED DESCRIPTION

Figure 3:
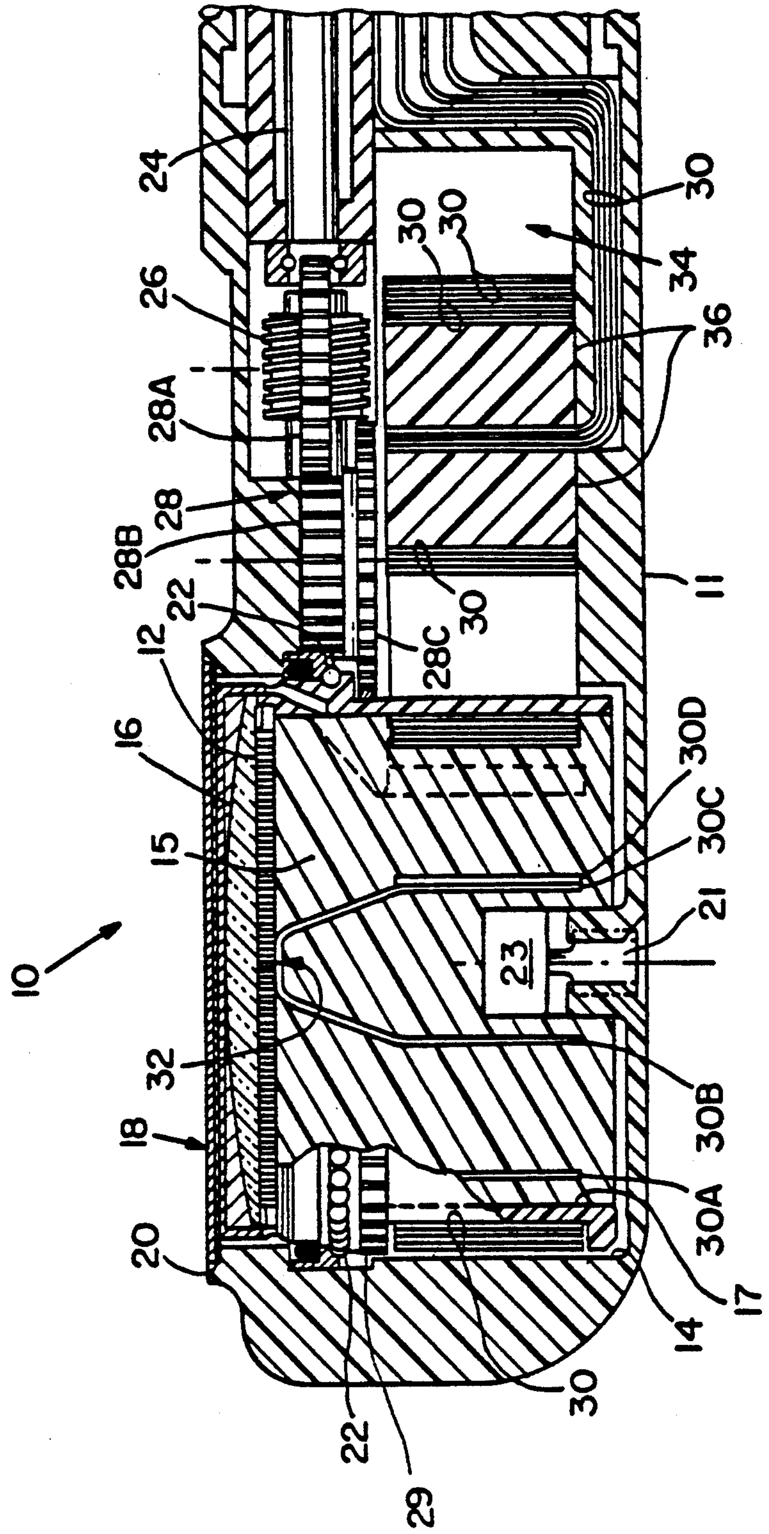
FIG. 3 is a longitudinal cross-sectional view of an ultrasound probe in accordance with the present invention.

A transesophageal ultrasound probe illustrating the principles of the present invention is shown in FIG. 3. The probe 10 has a probe housing 11 shaped for insertion into a subject's esophagus. A rotatable transducer array 12 of piezoelectric elements is positioned on a support structure 17 within an inner volume 14 at the distal end of the probe. By rotating the array, two-dimensional cross-sectional images of a subject may be obtained along a variety of scan planes.

Figure 2A:
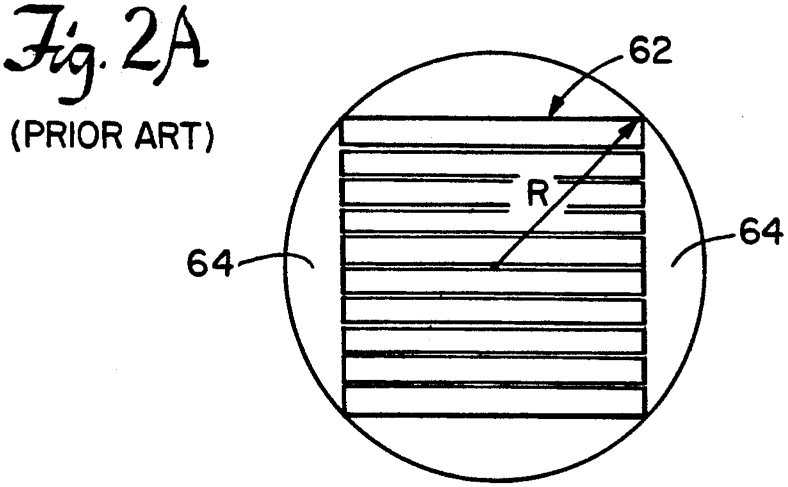
FIG. 2A is a plan view of a conventional rotatable transducer array having a square shape.

In conventional transesophageal imaging systems, a probe comprises an array formed of a plurality of transducer elements arranged in a plane and having uniform mechanical lengths. In other words, the surface of the array has a square or rectangular shape. Where it is desireable to rotate such arrays, problems arise due to the inefficient shape of these arrays. These problems are nearly identical with respect to square arrays and rectangular arrays, so only a square array will be discussed hereinafter. A conventional array having a square shape 62 is shown in FIG. 2A. When it is desirable to rotate this square array, it is positioned to rotate within an inner volume of the probe having a generally circular cross-sectional area equal to $\pi R^2$, where R is the radius circular area. For the square array 62 to rotate freely within the cross-sectional area about an axis through its center, the greatest length of the square array from the center of rotation must be no larger than R. With this configuration, the surface area of the square array is at most $2R^2$, which is less than 64% of the available area of the circular cross-section of the inner volume in the plane of the array. As a result, gaps 64 exist between the sides of the array and the inner volume. Thus, a square rotatable array inefficiently utilizes the circular area of radius R of the inner volume in the plane of the array required for rotation.

Figure 1B:
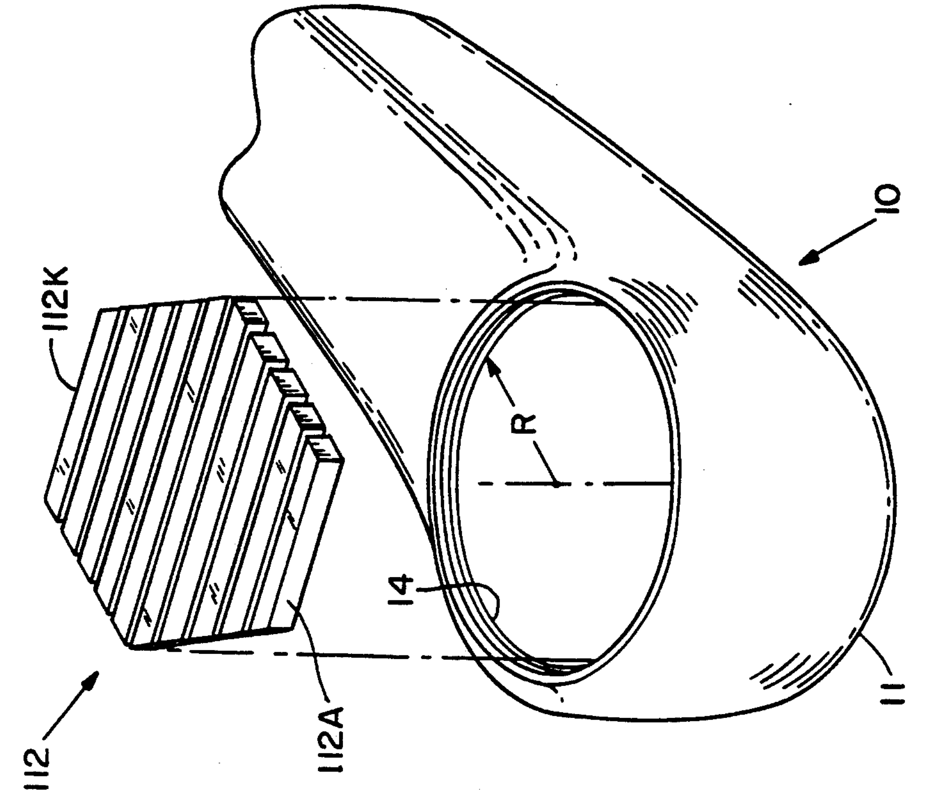
FIG. 1B is a partial perspective view illustrating a representative alternate embodiment of a rotatable transducer array.
Figure 1A:
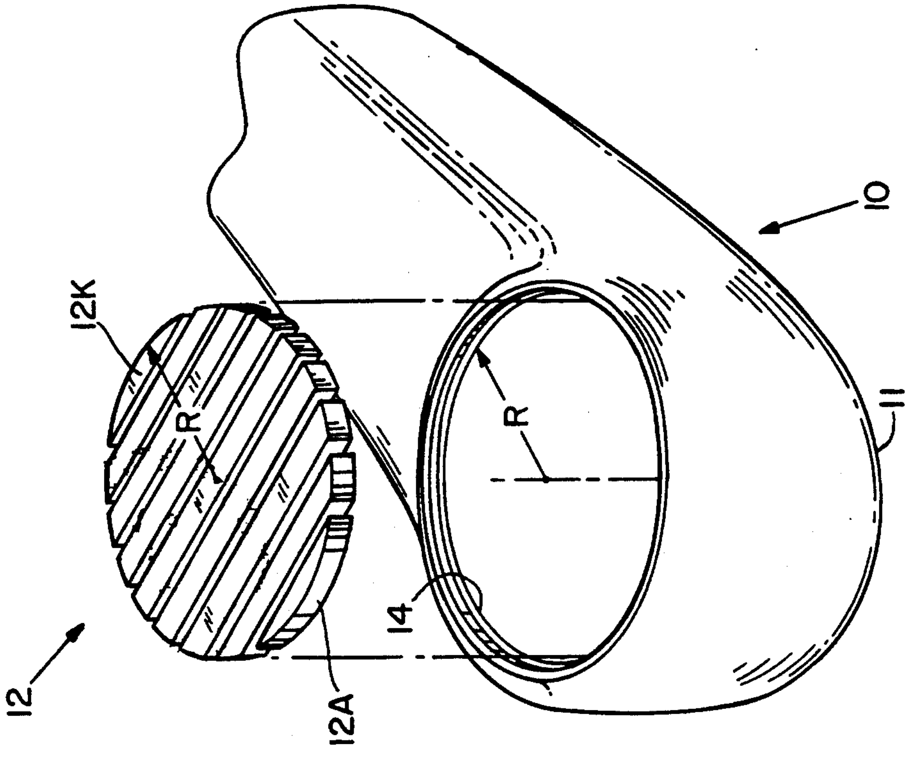
FIG. 1A is a partial perspective view illustrating a preferred embodiment of a rotatable transducer array of the present invention.

A TEE probe comprising a circular rotatable ultrasound transducer array 12 of the present invention is shown in FIG. 1A. The array is positioned within the inner volume 14 of the probe housing 10. The array 12 comprises a plurality of elongated piezoelectric transducer elements 12A–12 K which are arranged in a plane. Typically, the array 12 has at least 64 elements. In accordance with this invention, the transducer elements of the array 12 have different mechanical lengths and are arranged such that the array has a circular shape.

One advantage of the present invention is that the circular shaped array has the maximum allowable surface area of any array capable of rotating within cross-sectional area of the inner volume. Referring to FIG. 1A, the inner volume 14 has a circular cross-sectional area equal to $\pi R^2$, where R is the radius of the circular region. In accordance with the present invention, the rotatable array 12 has a circular shape transmitting/receiving surface with radius substantially equal to R and a transmitting surface area substantially equal to $\pi R^2$. As such, the circular array 12 rotates within the inner volume about an axis through the center of rotation, while occupying substantially all of the entire available cross-sectional area in the inner volume 14. In other words, the rotatable circular array 12 utilizes 100% of the available area for rotation within the inner volume can be minimized such that the overall size of the probe can be reduced.

Figure 2B:
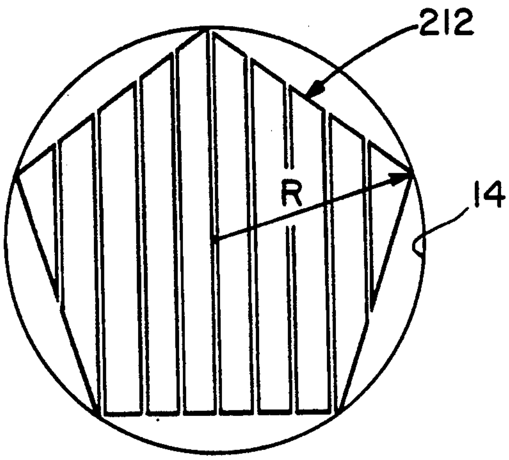
FIG. 2B is a plan view of a representative alternative embodiment rotatable transducer array having a pentagonal shape.

In an alternative embodiment of the present invention, a rotatable array has a pentagonal-shaped surface as shown in FIG. 2B. The array 212 comprises a plurality of elongated piezoelectric transducer elements which are arranged in a plane. The transducer elements have different mechanical lengths and are arranged such that the array has a pentagonal-shaped transmitting/receiving surface. As in the preferred embodiment, the array is positioned within an inner volume 14 of the probe housing.

Like the preferred embodiment, the pentagonal array 212 is shaped to more efficiently utilize a given cross-sectional area within the inner volume 14. Once again, the circular cross-sectional area of the inner volume 14 has a radius R and an area equal to $\pi R^2$. The maximum length of the array 212 from the center of rotation substantially equal to R, such that the array may rotate freely within the inner volume 14. Accordingly, the pentagonal array has a surface area approximately equal to $2.4(R^2)$. Thus, the rotatable pentagonal array utilizes 76% of the available area of the inner volume, resulting in a 19% improvement over a conventional square array.

Figure 2C:
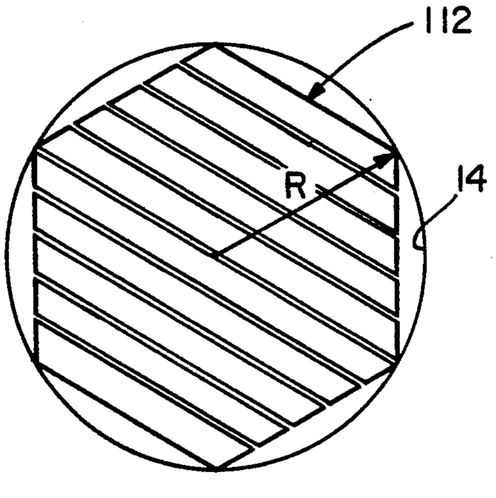
FIG. 2C is a plan view of the rotatable transducer array of FIG. 1B.

As shown in FIG. 1B and FIG. 2C, yet another alternative embodiment of the present invention comprises a rotatable hexagonal-shaped array 112. The array 112 is formed of a plurality of transducer elements 112A–112K arranged in a plane. The elements have different mechanical lengths such that the transmitting/receiving surface of the array has a hexagonal shape. The hexagonal array is positioned to rotate within an inner volume 14 of the probe housing 11. As in the other embodiments, the circular cross-sectional area of the inner volume 14 has a radius R and an area equal to $\pi R^2$. For the array 112 to rotate within the inner volume, the maximum radius of the array from the center of rotation is slightly less than R such that the array has a transmitting surface area substantially equal to $2.6(R^2)$. As a result, the rotatable hexagonal array 112 utilizes about 83% of the available area in the inner housing, translating to a 30% improvement over the conventional square array. The hexagon array is preferred over the pentagonal array not only because of the increased percentage of area utilized. As shown in FIG. 2C, it also allows for a preferred dual symmetric array, i.e. symmetric relative to two perpendicular axes intersecting at the center of the array.

Figure 2D:
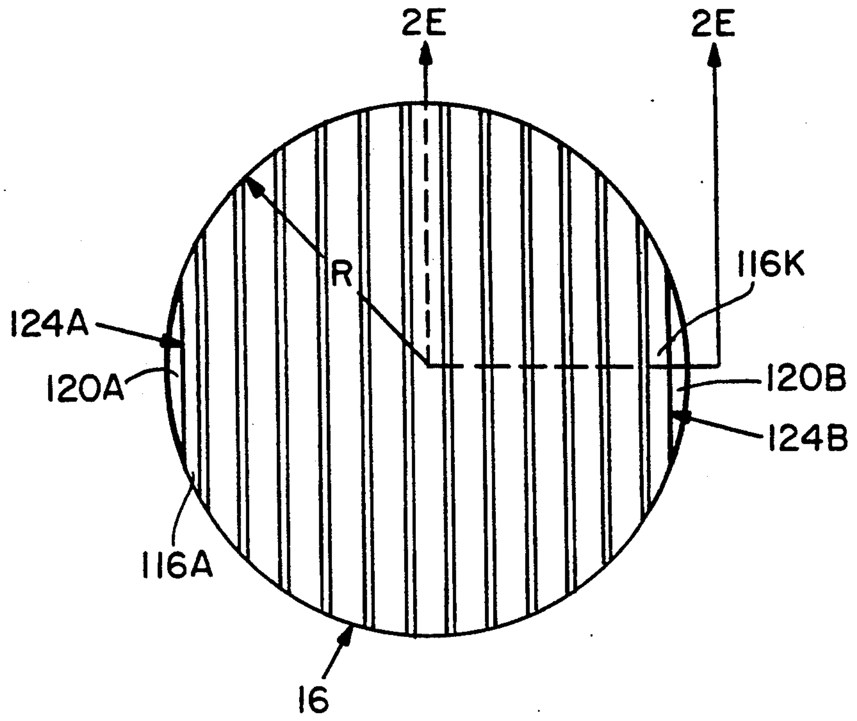
FIG. 2D is a plan view of an alternative embodiment rotatable transducer array having a substantially circular shape.
Figure 2E:
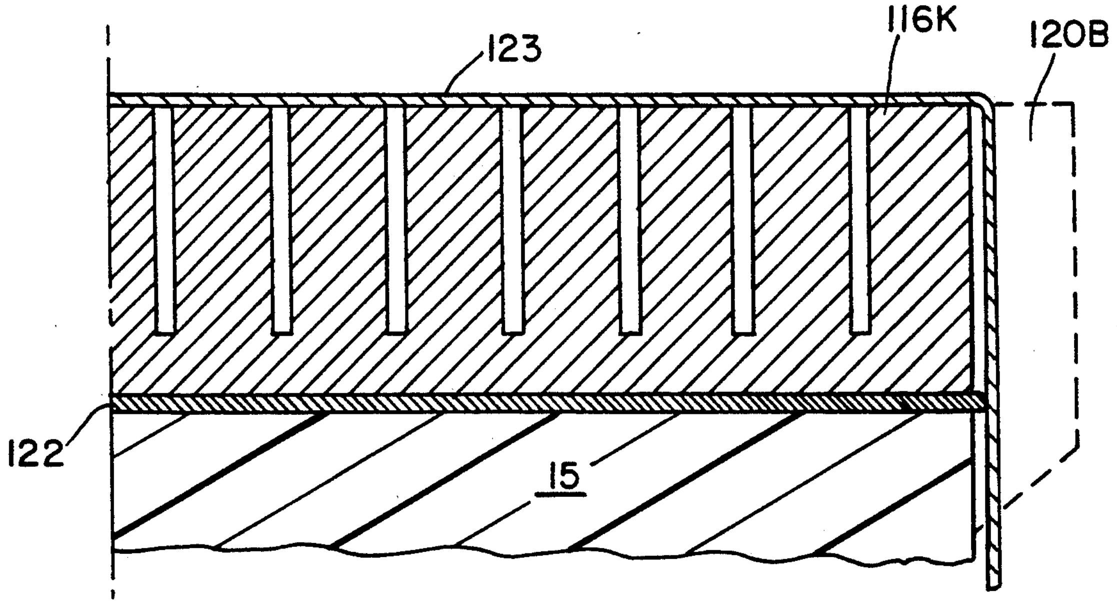
FIG. 2E is an enlarged partial cross-sectional view of the substantially circular rotatable transducer array of FIG. 2D taken along the line 2E—2E.

Another alternative embodiment comprising a substantially circular array is shown in FIGS. 2D and 2E. The array 116 is formed of a plurality of transducer elements 116A–116K arranged in a plane. Preferrably, the outermost elements 116A and 116K are active transducer elements. Alternatively, the outermost elements may be inactive mechanical buffers for protecting the active transducer elements from damage during fabrication.

The substantially circular array 116 is fabricated in accordance with the following process. A flex circuit 122 is bonded to one side of a solid crystal. The crystal is placed in a mold comprising a mass of acoustic damping material 15 such that the flex circuit is encapsulated in the damping material. After removing the resulting structure from the mold, the crystal is cut to form the individual transducer elements 116A–116K. Furthermore, "D" shaped sections 120A and 120B are milled or cut off the elements 116A and 116K respectively to expose a flex circuit 122 located beneath the elements (see FIGS. 2D and 2E). The ground signal lines on exposed flex circuit are coupled to a metal film 123 which is linked to the common ground plane for the array (not shown). As a result of the "D" shaped cuts, the array has a pair of edges (124A and 124B) along its periphery symmetrically disposed about an axis through the center of the array in the plane of the transducer elements. Since the edges are straight, the metal film closely conforms to the array while extending to the ground lines of the flex circuit.

Like the other embodiments, the array 116 is positioned to rotate within an inner volume 14 of the probe housing 11. For the array to rotate within the inner volume having a radius R, the maximum radius of the array 116 from the center of rotation is slightly less than R. Accordingly, the array has a transmitting surface area approximately equal to $3.0(R^2)$. Thus, the substantially circular array 116 utilizes about 94% of the available cross-sectional area in the inner housing, translating to a 50% improvement over a square array.

It should be understood that the polygonal shaped arrays of FIG. 2B and 2C are merely representative alternative embodiments of the present invention. The present invention more generally comprises a rotatable array, which during rotation defines a circular region of rotation having a radius R from an axis perpendicular to the elements of the array, the array having a surface area which substantially matches the area of the circular region of rotation. In other words, the rotatable array of the present invention has an N-sided polygonal shaped transmitting/receiving surface, where N is an integer greater than four. For example, the rotatable array has a pentagonal shaped transmitting surface for N equals five. As explained earlier, the pentagonal array utilizes 76% of the circular region of rotation which represents a 19% improvement over conventional shaped arrays. For N equals six, the array has a hexagonal shaped surface, utilizing about 83% of the circular region of rotation and providing a 30% improvement over conventional shaped arrays. To that end, as N approaches infinity the rotatable array resembles a circular shaped array which utilizes 100% of the circular region of rotation, as explained in the preferred embodiment.

A longitudinal cross-sectional view of an ultrasound probe illustrating the principles of the present invention is shown in FIG. 3. The probe 10 has a probe housing 11 shaped for insertion into a subject's esophagus. In the preferred embodiment, the circular rotatable transducer array 12 is positioned on a support structure 17 within the inner volume 14 located at the distal end of the probe. Alternatively, the array may have a polygonal shape surface area as explained above.

A cylindrical lens 16 covering the rotatable array 12 serves to focus the energy emitted by the array along a plane which is parallel to the array elements. Additionally, the energy emitted from the array is electronically focused in a plane perpendicular to the plane of the array elements. A stationary cover assembly 18 is mounted over the inner housing 11 above the array. The cover assembly prevents undesirable substances from touching the lens. A layer of grease 20, located between the lens 16 and the cover 18, serves as a transmission medium.

The array is electrically connected to a flexible cable assembly 30 for communications with the remote ultrasound imaging electronics (not shown). More specifically, the flexible cable assembly extends from the array, through the inner volume 14 and a rear volume 34, to a plurality of individual conductors (not shown) which are coupled to the remote ultrasound electronics.

In one embodiment, the flexible cable assembly is a single flex cable comprising a plurality of flex cables extensions 30A–D, each having a plurality of signal lines printed thereon. The flex cables 30A and 30B are are integrally coupled as are flex cables 30C and 30D. A common section of each flex cable pair is attached to the underside of the array at 32 forming the single flex cable. A mass of nonconductive acoustical damping material 15 fills the volume within a support structure 17, encapsulating a portion of the flex cables. The acoustical damping material 15 absorbs acoustic signals from the back of the array.

The array 16 may be rotated about an axis extending through the center of the array and a shaft 21 for obtaining cross-sectional images along a variety of scan planes. To that end, the rotatable support structure 17 that supports the array is mechanically linked to a plurality of ball bearings 22 and to a bearing 23 at the shaft. Rotation of the array is achieved by a rotating cable 24 and a worm gear 26. More specifically, the rotating cable 24, resembling a speedometer cable, is mechanically linked to the worm gear 26. The rotation of the cable 24 causes the worm gear 26 to rotate about a common shaft. The worm gear is mechanically linked to a first gear 28A such that rotation of the worm gear causes the first gear to rotate about an axis which is parallel to the axis of rotation for the array. The first gear 28A is one of a plurality of gears 28 which are mechanically linked to each other and have parallel axes of rotation. Thus, the rotation of the worm gear drives the first gear 28A, the rotation of first gear drives the second gear 28B, the rotation of the second gear drives the third gear 28C. The third gear is mechanically linked to a ring gear 29 which is coupled to the support structure 17. Thus, the rotation of the third gear causes the ring gear to turn such that the array rotates.

While this invention has been particularly shown and described above with references to specific embodiments, the foregoing and other changes in form and detail may be made by one skilled in the art without departing from the spirit and scope of the invention.

We claim:

1. An ultrasound probe for use with ultrasound imaging electronics in echo cardiography comprising:
   - a probe housing;
   - a rotatable ultrasound array positioned within a volume in the probe housing, the array comprising a plurality of elongated piezoelectric transducer elements arranged in parallel in a plane, each transducer element having a mechanical length which differs with respect to other transducer elements, the array being rotatable within the probe housing about an axis perpendicular to the plane of the transducer elements and the rotating array defining a circular region of rotation about the axis, the array having a surface area in the plane of the transducer elements which substantially matches the area of the circular region of rotation;
   - a cable for electrically connecting the array with ultrasound imaging electronics; and
   - a drive mechanism for rotating the array.

2. An ultrasound probe as claimed in claim 1 wherein the transducer elements are arranged such that the rotatable array has a circular shape in the plane of said transducer elements.

3. An ultrasound probe as claimed in claim 1 wherein the transducer elements are arranged such that the rotatable array has an N-sided polygonal shape in the plane of said transducer elements, N being an integer greater than four.

4. An ultrasound probe as claimed in claim 1 in which the rotatable array has a surface area in the plane of the transducer elements which occupies at least eighty percent of the area of the circular region of rotation.

5. An ultrasound probe as claimed in claim 1 wherein the probe is adapted for insertion into a subject's esophagus.

6. An ultrasound probe as claimed in claim 1 wherein the cable is a flat cable attached to a backside of the array spaced from ends of said transducer elements.

7. An ultrasound probe as claimed in claim 1 wherein the cable is a flat cable attached to a backside of the array at substantially the centers of the transducer elements.

8. An ultrasound probe for use with ultrasound imaging electronics in echo cardiography comprising:
   - a probe housing;
   - a rotatable ultrasound array positioned within a volume in the probe housing, the array comprising a plurality of elongated piezoelectric transducer elements arranged in parallel in a plane, each transducer element having a mechanical length which differs with respect to other transducer elements the array being rotatable about an axis perpendicular to the plane of the transducer elements and the rotating array defining a circular region of rotation about the axis, the array having a surface area in the plane of the transducer elements which substantially matches the area of the circular region of rotation, the array having two flat edges along its periphery, the flat edges being symmetrically disposed about an axis through the center of the array and parallel to the transducer elements;

a cable for electrically connecting the array with ultrasound imaging electronics; and a drive mechanism for rotating the array.

9. An ultrasound probe as claimed in claim 8 in which the rotatable array has a surface area in the plane of the transducer elements which occupies at least ninety percent of the area of the circular region of rotation.

10. An ultrasound probe as claimed in claim 8 wherein the cable is a flat cable attached to a backside of the array spaced from ends of said transducer elements.

11. An ultrasound probe as claimed in claim 8 wherein the cable is a flat cable attached to a backside of the array at substantially the centers of the transducer elements.

12. An ultrasound probe for use with ultrasound imaging electronics in echo cardiography comprising:

a probe housing;

a rotatable ultrasound array positioned within a volume in the probe housing, the array comprising a plurality of elongated piezoelectric transducer elements arranged in parallel in a plane, each transducer element having a mechanical length which differs with respect to other transducer elements, the array being rotatable within about an axis perpendicular to the plane of the transducer elements and the rotating array defining a circular region of rotation about the axis, the array having a surface area in the plane of the transducer elements which substantially matches the area of the circular region of rotation;

a flat cable for electrically connecting the array with ultrasound imaging electronics, the flat cable being attached to a backside of the array spaced from ends of said transducer elements; and a drive mechanism for rotating the array.

* * * * *